United States Patent [19]

Horn et al.

[11] Patent Number: 5,684,215
[45] Date of Patent: Nov. 4, 1997

[54] ONE STAGE PROCESS FOR THE PREPARATION OF ALCOHOLS

[75] Inventors: Gerhardt Horn, Oberhausen; Carl Dieter Frohning, Wesel, both of Germany

[73] Assignee: Hoechst Aktiengesellschaft, Germany

[21] Appl. No.: 999,191

[22] Filed: Dec. 28, 1992

Related U.S. Application Data

[63] Continuation of Ser. No. 826,680, Jan. 27, 1992, abandoned, which is a continuation of Ser. No. 589,374, Sep. 27, 1990, abandoned.

[30] Foreign Application Priority Data

Sep. 28, 1989 [DE] Germany .......................... 39 32 332.3

[51] Int. Cl.$^6$ .................................................. C07C 29/14
[52] U.S. Cl. ............................................ 568/881; 568/883
[58] Field of Search ...................................... 568/881, 883

[56] References Cited

U.S. PATENT DOCUMENTS

| 2,983,734 | 5/1961 | Sargent ................................. 549/503 |
| 3,978,149 | 8/1976 | Mertzweiller et al. .................. 585/277 |
| 4,271,323 | 6/1981 | Durand et al. . | |

FOREIGN PATENT DOCUMENTS

| 759121 | 8/1980 | Switzerland . |
| 1384329 | 3/1988 | Switzerland . |

*Primary Examiner*—Rebecca Cook
*Attorney, Agent, or Firm*—Bierman, Muserlian and Lucas LLP

[57] ABSTRACT

A process for the preparation of alcohols by reaction of organic carbonyl compounds or mixtures containing them with hydrogen over a supported catalyst containing nickel, aluminum oxide, and zirconium dioxide at elevated temperature and, if appropriate, under elevated pressure. Ketones, aldehydes and derivatives thereof are reacted as the carbonyl compounds at temperatures of 60° to 150° C.

22 Claims, No Drawings

ONE STAGE PROCESS FOR THE PREPARATION OF ALCOHOLS

This application is a continuation of application Ser. No. 07/826,680 filed Jan. 27, 1992, now abandoned, which is a continuation of application Ser. No. 07/589,374, filed Sep. 27, 1990, now abandoned.

This Application claims the priority of German Application P 39 32 332.3, filed Sep. 28, 1989.

The present invention relates to a process for the preparation of alcohols starting from organic carbonyl compounds or mixtures containing them.

BACKGROUND OF THE INVENTION

It is known that organic carbonyl compounds can be reacted with hydrogen in the presence of a hydrogenation catalyst at elevated temperatures and, if appropriate, under increased pressure to produce the corresponding alcohols. The reaction can be carried out either batchwise or continuously in a homogeneous or heterogeneous phase system. The hydrogenation catalyst is accordingly present either as a solution, in finely divided form as a suspension, or as a fixed bed contact catalyst in the form of pieces. The carbonyl compounds to be hydrogenated can be passed into contact with the catalyst in the gaseous or liquid state.

A comprehensive description of the preparation of alcohols by catalytic hydrogenation of carbonyl compounds, in particular of ketones, aldehydes and derivatives thereof, can be found in Houben-Weyl, Methoden der organischen Chemie (Methods of Organic Chemistry), Georg Thieme Verlag Stuttgart-New York 1984, Volume VI/1b pages 9 to 111.

DE-AS 12 70 018 describes a process for the preparation of alcohols by catalytic hydrogenation of aldehydes in the presence of a suspended catalyst, the gaseous hydrogen being added to the reaction at a rate such that the catalyst is suspended in only part of the liquid phase. The liquid phase containing no catalyst is removed continuously; Raney nickel is used as a particularly suitable catalyst for carrying out this process.

DE-AS 12 31 227 relates to a process for the preparation of alcohols by continuous hydrogenation of aldehydes having 6 to 13 carbon atoms in the liquid phase using an amorphous nickel catalyst.

DE-OS 26 28 987 describes a process for the preparation of alcohols having 3 to 5 carbon atoms by reaction of the corresponding aldehydes in the liquid phase over a supported catalyst containing nickel, copper, and manganese.

The processes described above for the preparation of alcohols leaves something to be desired in respect of the conversion and/or selectivity of the catalytic hydrogenation reaction. Furthermore, they require relatively long reaction times and high reaction temperatures. There is therefore a need for improvement of the prior art processes.

DESCRIPTION OF THE INVENTION

The object of the invention is achieved by a process for the preparation of alcohols by reaction of organic carbonyl compounds or mixtures containing them with hydrogen in the presence of a hydrogenation catalyst at elevated temperature and, if appropriate, under increased pressure. The reaction is carried out at 60° to 150° C. over a supported catalyst containing nickel, aluminum oxide, and zirconium dioxide.

Compared with processes according to the prior art, the invention enables the hydrogenation of carbonyl compounds to be carried out, not only with an increased conversion, but also with an increased selectivity in many cases. Furthermore, it allows the hydrogenation to proceed at lower temperatures and/or with shorter reaction times, i.e. with higher throughputs, in comparison with known procedures. The process according to the invention can be used for the conversion of ketones, ketone derivatives, aldehydes and derivatives thereof.

Ketones which can be employed are acetone, methyl ethyl ketone, diethyl ketone, hexanones, for example cyclohexanone, heptanones and octanones, and also higher ketones, as well as aromatic ketones, such as acetophenone and benzophenone. Examples of ketone derivatives which can be employed are acetol (hydroxyacetone), acetoin (acetylmethylcarbinol), dihydroxyacetone, benzoin, and lactones, as well as ketoses, such as fructose.

Aromatic, araliphatic, cycloaliphatic, and aliphatic aldehydes and derivatives thereof, can be converted with the aid of the process according to the invention. The cycloaliphatic and aliphatic compounds and their derivatives are preferred, the aliphatics and derivatives thereof being most preferred. The use of aliphatic straight and branched chain aldehydes having 2 to 18 carbon atoms is of particular importance. With the exception of acetaldehyde, these aldehydes can be prepared, for example, by hydroformylation of olefins. They can be employed in the process according to the invention in prepurified form, and also as the crude product, for example, as as the crude hydroformylation product.

Suitable aldehydes are: acetaldehyde, propanal, butanal, pentanal, hexanal, heptanal, octanal, nonanal, decanal, and alkanals having 11 to 18 carbon atoms, in particular acetaldehyde, propanal, butanal, pentanal, octanal, nonanal, and alkanals having 11 to 18 carbon atoms, most preferably propanal, butanal, octanal and nonanal. All of the foregoing are of the normal or iso forms.

Unsaturated aldehydes can also be converted according to the invention. These include: acrolein, crotonaldehyde, n- and i-pentenal, n- and i-hexenal, n- and i-heptenal and n- and i-octenal, in particular acrolein, crotonaldehyde and 2-ethylhexenal, most preferably, 2-ethylhexenal.

The aldehyde derivatives can be prepared by a number of customary syntheses; e.g. aldolization, aldol condensation, and substitution or addition reactions—the addition of water onto unsaturated aldehydes may be mentioned—and can be converted according to the invention into the corresponding alcohols with good results.

Mixtures containing organic carbonyl compounds are advantageously solutions of the carbonyl compounds listed above and also crude reaction products such as are obtained in the preparation of the carbonyl compounds; e.g. by aldolization, aldol condensation, hydroformylation, substitution, or addition. The invention is particularly useful in connection with dilute solutions. Therefore, even though such mixtures often contain the carbonyl compounds in reduced and extremely low concentrations, they can be converted according to the invention into the corresponding alcohols with good results.

The hydrogenation catalyst contains 20 to 90% by weight of nickel, based on the catalyst composition, and 1 to 30, in particular 3 to 15, preferably 4 to 10 parts by weight of aluminum oxide and 0.5 to 20, in particular 1 to 10, preferably 1.5 to 5 parts by weight of zirconium dioxide, in each case per 100 parts by weight of nickel, as a coprecipitate on a support material.

PREPARATION OF THE CATALYST

An aqueous Ni—Al—Zr mixed salt solution is mixed with an aqueous solution of a basic compound as a precipitating agent, the basic compound being employed in a stoichiometric excess of 5 to 100%, based on the amount required for quantitative precipitation of Ni, Al, and Zr. Ni, Al, and Zr are precipitated simultaneously at 60° to 120° C. and pH 7 to 10 and deposited as a coprecipitate on a support material.

In order to prevent undesirable hydrolysis and to improve the precipitation, it is advisable that free acid be added to the mixed salt solution in an excess corresponding to a ratio of $H^+:Zr^{4+}=2$ to 40:1, in particular 3 to 30:1, preferably 4 to 20:1. The free acid is determined by titration with NaOH (end point pH=0.8). Hydrochloric acid, sulfuric acid and preferably nitric acid can be employed as the free acid.

The mixed salt solution consists of 10 to 100, in particular 20 to 80, preferably 30 to 50 g of Ni/liter. It contains aluminum corresponding to 1 to 30, in particular 3 to 15, preferably 4 to 10 parts by weight of $Al_2O_3$ per 100 parts by weight of Ni. It also contains zirconium corresponding to 0.5 to 20, in particular 1 to 10, preferably 1.5 to 5 parts by weight of $ZrO2$ per 100 parts by weight of Ni.

The mixed salt solution is prepared by dissolving water-soluble inorganic, organic, or complex salts of nickel, zirconium, and aluminum, in particular sulfates, chlorides, acetates, and nitrates thereof, preferably nitrates thereof, in water.

The precipitating agent is advantageously an aqueous solution of a basic compound, in particular an aqueous alkali metal carbonate, alkali metal bicarbonate, alkali metal hydroxide, ammonium hydroxide, or ammonium carbonate solution, which has a pH of 7.5 to 13, in particular 8 to 12, preferably 9 to 11. Aqueous solutions containing 0.3 to 1.5, in particular 0.8 to 1.2 mol of alkali metal carbonate/1 of solution produce quite good results.

In order to ensure that the precipitation be as complete as possible to form a particularly homogeneous coprecipitate, the basic compound is employed in a stoichiometric excess of 5 to 100, in particular 10 to 70, preferably 20 to 40%, in each case based on the amount of basic compound required for complete precipitation of Ni, Al and Zr. The precipitation is brought about either by bringing together and mixing the mixed salt solution and the precipitating agent continuously or, according to a preferred variant, by initially introducing the precipitating agent into the vessel and introducing the mixed salt solution into the precipitating agent.

The support material can be employed in the reaction with the mixed salt solution and/or with the precipitating agent. It has proved to be particularly advantageous to first mix the mixed salt solution and the precipitating agent with one another and then to add the support material. Suitable support materials are active charcoal, aluminas, pumice, γ-$Al_2O_3$, $SiO_2$, silica gel, kieselguhr, and silicic earths. $SiO_2$, silica gel, kieselguhr and silicic earth have proved to be particularly suitable. Kieselguhr and $SiO_2$ in the form of precipitated silicic acid are preferably employed. 6 to 80, in particular 15 to 65, preferably 35 to 50 parts by weight of support material are usually employed per 100 parts by weight of Ni.

To prepare homogeneous coprecipitates, a pH range of 7 to 10, in particular 7.3 to 9, preferably 7.5 to 8.5, and a temperature of 60° to 120°, in particular 70° to 110°, preferably 95° to 105° C. are maintained during the precipitation.

When the precipitation is complete, after cooling, if appropriate, the mixture is filtered and the product is washed, shaped as required, and then dried and reduced. Drying is carried out between 40° and 120°, in particular 50° and 100° C.

The reduction by means of hydrogen is carried out at 300° to 550° C., a degree of reduction of at least 80%, in particular at least 90%, preferably 95% or more, being desired. The degree of reduction is understood as the ratio of the content of nickel metal: total nickel content×100%.

The process according to the invention for the preparation of alcohols by reaction of organic carbonyl compounds with hydrogen in the presence of the catalyst described above can be carried out batchwise or continuously.

THE LIQUID PHASE

If the process is carried out in the liquid phase, the catalyst can be employed either as a finely divided suspension or in the form of pieces as a fixed bed contact catalyst. The reaction temperature is 60° to 150° C. If particularly gentle conditions are required, a reaction temperature of 60° to 80° C. is used. In most cases, the hydrogenation according to the invention can be carried out at temperatures of 80° to 140° C., in particular 90° to 130° C., preferably 100° to 125° C. The pressure is usually 0.1 to 25, in particular 1.0 to 15, preferably 2.0 to 10 MPa.

The carbonyl compound to be reacted is either passed in liquid form, together with hydrogen, batchwise or continuously to the suspended catalyst, or the feed material containing the carbonyl compound is passed con- or counter-currently with hydrogen over the supported catalyst containing nickel, aluminum oxide, and zirconium oxide, which is in the form of pieces and arranged as a fixed bed. When carrying out the process according to the invention industrially, the fixed bed procedure will probably often be preferred, the feed mixture being passed over the catalyst either from the top downwards (trickle) or from the bottom upwards (sump). If the trickle method is used, the hydrogen is passed con- or countercurrent, preferably concurrently, with the feed material. If the sump method is to be practiced, the hydrogen is advantageously passed concurrently with the feed mixture over the supported catalyst.

If the process is carried out continuously in the liquid phase, the space velocity, expressed as the volume of liquid feed material/volume of catalyst per hour (V/Vh), is 0.6 to 2.0, in particular 0.8 to 1.6, preferably 1.0 to 1.5.

An amount of hydrogen corresponding to at least the stoichiometry of the reaction must be employed. As a rule, however, a stoichiometric excess of hydrogen will be used in order to favorably influence the reaction. An excess of hydrogen of 1 to 100, in particular 2 to 50, preferably 5 to 10 mol per equivalent of carbonyl compounds is sufficient for carrying out the hydrogenation in the liquid phase. Unreacted hydrogen can be recycled back to the reaction.

THE GAS PHASE

However, the process according to the invention may also be carried out in the gas phase; the feed material is passed over the catalyst in the gaseous state, together with hydrogen, over the supported fixed bed catalyst. The reaction in the gas phase is carried out at 60° to 150° C. In most cases, a temperature of 80° to 140° C., in particular 90° to 130° C. is sufficient. The pressure is 0.05 to 2.0, in particular 0.1 to 1.2, preferably 0.15 to 1.0 MPa.

If the process is carried out continuously in the gas phase, the space velocity, expressed as the volume of liquid feed material/volume of catalyst per hour (V/Vh), is 0.2 to 1.5, in particular 0.3 to 1.2, preferably 0.5 of 1.0.

An amount of hydrogen corresponding at least to the stoichiometry of the reaction must be employed. However, a stoichiometric excess of hydrogen is usually used in order to guide the reaction in the desired direction. An excess of hydrogen of 0.5 to 50, in particular 1 to 20, preferably 2 to 10 mol per equivalent of carbonyl compound proves to be adequate for the gas phase hydrogenation. Unreacted hydrogen can be recycled into the reaction.

The procedure used depends, on the one hand, on the nature of the carbonyl compound and, on the other hand, on the apparatuses available in which the reaction is to be carried out. No general recommendation giving one of the process variants illustrated above preference can be stated in view of the wide possibilities of use of the process of the invention.

The examples listed below demonstrate the present invention without limiting it.

EXAMPLE 1

400 g of n-butanal and 2.4 g of a catalyst which contains 100 parts by weight of Ni, 5 parts by weight of aluminum oxide and 3 parts by weight of zirconium dioxide as a coprecipitate and 40 parts by weight of $SiO_2$ as the support are initially introduced into an autoclave (volume 1000 ml) provided with a magnetic piston stirrer, with exclusion of air. Hydrogen is then forced in, the mixture is heated with stirring, and the desired pressure is established by control of the addition of hydrogen. The reaction is interrupted as soon as no further uptake of hydrogen occurs (hydrogenation time).

| Reaction conditions | |
| --- | --- |
| Pressure | 7.0 MPa |
| Temperature | 115° C. |
| Hydrogenation time | 70 minutes |

The hydrogenation product has a CO number of only 1.2 (mg of KOH/g), corresponding to 0.15% by weight of n-butanal.

COMPARISON EXAMPLE 1

The procedure is as in Example 1, except that a customary catalyst, without any $Al_2O_3$ or $ZrO_2$, containing about 55% by weight of Ni and about 30 to 35% by weight of $SiO_2$ is used.

| Reaction conditions | |
| --- | --- |
| Pressure | 7.0 MPa |
| Temperature | 115° C. |
| Hydrogenation time | 100 to 120 minutes |

The hydrogenation product has a CO number of 1.5 (mg of KOH/g), corresponding to 0.2% by weight of n-butanal.

EXAMPLE 2

400 g of a mixture which, corresponding to a CO number of 126 (mg of KOH/g), contains about 29% by weight of octanal (prepared by hydroformylation of heptene) and unsaturated compounds corresponding to an iodine number of 16.1 (g of $I_2$/100 g) and 12.5 g of the catalyst used in Example 1 are initially introduced into an autoclave (volume 100 ml) provided with a magnetic piston stirrer. The procedure is then as described in Example 1.

| Reaction conditions | |
| --- | --- |
| Pressure | 8.0 MPa |
| Temperature | 120° C. |
| Hydrogenation time | 60 minutes |

The hydrogenation product has a CO number of only 0.5 (mg of KOH/g), corresponding to 0.1% by weight of octanal, and an iodine number of 2.5 (g of $I_2$/100 g).

COMPARISON EXAMPLE 2

The procedure is as in Example 2, except that a customary catalyst, with no nickel-aluminum oxide-zirconium dioxide coprecipitate, containing about 65% by weight of Ni is used.

| Reaction conditions | |
| --- | --- |
| Pressure | 8.0 MPa |
| Temperature | 120° C. |
| Hydrogenation time | 75 minutes |

The hydrogenation product has a CO number of 3.2 (mg of KOH/g), corresponding to 0.8% by weight of octanal, and an iodine number of 12.5 (g of $I_2$/100 g).

EXAMPLE 3

400 g of a mixture which, corresponding to a CO number of 234 (mg of KOH/g), contains about 59% by weight of i-nonanal (prepared by hydroformylation of diisobutylene) and unsaturated compounds corresponding to an iodine number of 36 (g of $I_2$/100 g) and 7.5 g of the catalyst used in Example 1 are initially introduced into an autoclave (volume 1000 ml) provided with a magnetic piston stirrer. The procedure is then as described in Example 1.

| Reaction conditions | |
| --- | --- |
| Pressure | 8.0 MPa |
| Temperature | 120° C. |
| Hydrogenation time | 60 to 70 minutes |

The hydrogenation product has a CO number of 0.2 to 0.3 (mg of KOH/g), corresponding to 0.1% by weight of i-nonanal, and an iodine number of 0.2 to 0.3 (g of $I_2$/100 g).

COMPARISON EXAMPLE 3

The procedure is as in Example 3, except that the catalyst used in Comparison Example 1 is employed.

| Reaction conditions | |
| --- | --- |
| Pressure | 8.0 MPa |
| Temperature | 120° C. |
| Hydrogenation time | 85 minutes |

The hydrogenation product has a CO number of 0.5 to 0.6 (mg of KOH/g), corresponding to 0.2 to 0.3% by weight of i-nonanal, and an iodine number of 12 (g of $I_2$/100 g).

EXAMPLE 4

400 g of a mixture which, in addition to 1.2% by weight of n-propanol, 8.1% by weight of by-products, and about 83% by weight of i-butanol+water, also contains about 7.5% by weight of β-hydroxypropanal (determined by gas chromatographic analysis) and 6.7 g of the catalyst used in Example 1, are initially introduced into an autoclave (volume 1000 ml) provided with a magnetic piston stirrer. The procedure is then as described in Example 1.

| Reaction conditions | |
| --- | --- |
| Pressure | 8.0 MPa |
| Temperature | 90° C. |
| Hydrogenation time | 40 minutes |

The hydrogenation product has a CO number of 0.78 (mg of KOH/g), corresponding to <0.1% by weight of β-hydroxypropanal. According to analysis by gas chromatography, it has the following composition:

| | |
| --- | --- |
| First runnings | 0.1% by weight |
| n-Propanol | 1.3% by weight |
| By-products | 7.3% by weight |
| β-Hydroxypropanal | <0.1% by weight |
| Propane-1,3-diol | 7.7% by weight |
| i-Butanol + water | 83.5% by weight |

COMPARISON EXAMPLE 4

The procedure is as in Example 4, except that the catalyst used in Comparison Example 1 is employed.

| Reaction conditions | |
| --- | --- |
| Pressure | 8.0 MPa |
| Temperature | 90° C. |
| Hydrogenation time | 210 minutes |

According to analysis by gas chromatography, the hydrogenation product has the following composition:

| | |
| --- | --- |
| First runnings | 0.1% by weight |
| n-Propanol | 1.4% by weight |
| By-products | 9.4% by weight |
| β-Hydroxypropanal | <0.1% by weight |
| Propane-1,3-diol | 7.3% by weight |
| i-Butanol + water | 81.8% by weight |

As a comparison of Example 4 and Comparison Example 4 shows, according to the invention, the reaction of β-hydroxypropanal takes place in a considerably shorter time with at the same time less formation of by-products.

EXAMPLE 5

400 g of a mixture which, corresponding to a CO number of 12.7 (mg of KOH/g), contains predominantly n-butanol, and 1.6% by weight of n-butanal and unsaturated compounds corresponding to an iodine number of 2 to 4 (g of I$_2$/100 g) and 25 g of the catalyst used in Example 1 are initially introduced into an autoclave (volume 1000 ml) provided with a magnetic piston stirrer. The procedure is then as described in Example 1.

| Reaction conditions | |
| --- | --- |
| Pressure | 8.0 MPa |
| Temperature | 115° C. |
| Hydrogenation time | 120 minutes |

The hydrogenation product has a CO number of 0.04 (mg of KOH/g), corresponding to 0.005% by weight of n-butanal, and an iodine number of 0.01 (g of I$_2$/100 g).

COMPARISON EXAMPLE 5

The procedure is as in Example 5, except that the catalyst used in Comparison Example 1 is employed.

| Reaction conditions | |
| --- | --- |
| Pressure | 8.0 MPa |
| Temperature | 115° C. |
| Hydrogenation time | 120 minutes |

The hydrogenation product has a CO number of 1.95 (mg of KOH/g), corresponding to 0.25% by weight of n-butanal, and an iodine number of 0.17 (g of I$_2$/100 g).

EXAMPLE 6

Continuous Hydrogenation in the Liquid Phase

A vertical tube contains 1000 ml of the pelleted form of the catalyst used in Example 1. 1000 ml per hour of a liquid mixture which contains predominantly n-butanol and, corresponding to a CO number of 10 to 13 (mg of KOH/g), 1.3% to 1.8% by weight of n-butanal and unsaturated compounds corresponding to an iodine number of 1.5 to 2.4 (g of I$_2$/100 g) are passed over the catalyst from the bottom upwards concurrently with hydrogen.

| Reaction conditions | |
| --- | --- |
| Pressure | 8.0 MPa |
| Temperature | 105° C. |
| Hydrogen | 100 l (s.t.p.)/hour |

The hydrogenation product has a CO number of 0.1 to 0.5, corresponding to 0.012 to 0.06% by weight of n-butanal, and an iodine number of 0.01 (g of I$_2$/100 g).

COMPARISON EXAMPLE 6

Continuous Hydrogenation in the Liquid Phase

The procedure is as in Example 6, the vertical tube containing 1000 ml of the pelleted form of the catalyst used in Comparison Example 1. The same feed mixture as in Example 6 is passed over the bulk catalyst, but only in an amount of 250 to 300 ml per hour.

| Reaction conditions | |
| --- | --- |
| Pressure | 8.0 MPa |
| Temperature | 120° C. |
| Hydrogen | 25 to 30 l (s.t.p.)/hour |

The hydrogenation product has a CO number of 0.6 to 1.6 (mg of KOH/g), corresponding to 0.08 to 0.2% by weight of n-butanal.

As the direct comparison in Example 6 shows, the process according to the invention allows a throughput which is 3 to 4 times higher and, at the same time, a better conversion (demonstrated by the CO number) and lower reaction temperature.

EXAMPLE 7

Continuous Hydrogenation in the Liquid Phase

A vertical tube contains 1000 ml of the pelleted form of the catalyst used in Example 1. 1100 ml per hour of a liquid mixture which contains predominantly 2-ethyl-hexanol and, corresponding to a CO number of 4.9 (mg of KOH/g), 1.1% by weight of (2-ethylhexanal+2-ethylhexenal) and unsaturated compounds (including 2-ethylhexenal) corresponding to an iodine number of 1.6 (g of $I_2$/100 g) are passed over the catalyst from the top downwards concurrently with hydrogen.

| Reaction conditions | |
|---|---|
| Pressure | 2.5 MPa |
| Temperature | 115° C. |
| Hydrogen | 120 l (s.t.p.)/hour |

The hydrogenation product has a CO number of 0.041 (mg of KOH/g), corresponding to 0.009% by weight of (2-ethyl-hexanal+2-ethylhexenal) and an iodine number of 0.028 (g of $I_2$/100 g).

COMPARISON EXAMPLE 7

Continuous Hydrogenation in the Liquid Phase

The procedure is as in Example 7, the vertical tube containing 1000 ml of the pelleted form of the catalyst used in Comparison Example 1. 700 ml per hour of a liquid mixture which contains predominantly 2-ethylhexanol and, corresponding to a CO number of 3.0 to 3.7 (mg of KOH/g), 0.68 to 0.84% by weight of (2-ethylhexanal+2-ethylhexenal) and unsaturated compounds (including 2-ethylhexenal) corresponding to an iodine number of 1.6 (g of $I_2$/100 g) are passed over the catalyst from the top downwards concurrently with hydrogen.

| Reaction conditions | |
|---|---|
| Pressure | 2.5 MPa |
| Temperature | 130° C. |
| Hydrogen | 76 l (s.t.p.)/hour |

As the direct comparison in Example 7 shows, the process according to the invention allows a significantly higher throughput (that is to say V/Vh of 1.1, instead of V/Vh of 0.7) and, in spite of a lower reaction temperature, leads to a product of improved quality (demonstrated by the CO number and iodine number).

EXAMPLE 8

Continuous Hydrogenation in the Gas Phase

A vertical tube contains 1000 ml of the pelleted form of the catalyst used in Example 1. 500 ml per hour of a mixture which contains 65 to 75% by weight of n- and i-butanal, 8 to 15% by weight of n- and i-butanol, 3.5 to 5.5% by weight of n- and i-butyl formate, and 1 to 3% by weight of n- and i-dibutyl ether (determined by analysis by gas chromatography) are fed to a vaporizer. The mixture is passed in the gaseous state over the catalyst from the top downwards concurrently with hydrogen.

| Reaction conditions | |
|---|---|
| Pressure | 0.2 MPa |
| Temperature | 90° C. |
| V/Vh*: | 0.5 |
| Hydrogen | 2200 l (s.t.p.)/hour |

According to analysis by gas chromatography, the hydrogenation product contains 0.2 to 0.4% by weight of n- and i-butanal, 96.3 to 98.1% by weight of n- and i-butanol, 1.2 to 1.8% by weight of n- and i-butyl formate and 0.5 to 1.5% by weight of n- and i-dibutyl ether.

* Space velocity (volume of liquid feed material/volume of catalyst per hour)

While only a limited number of specific embodiments of the invention have been expressly disclosed it is, nonetheless, to be broadly construed and not to be limited except by the character of the claims appended hereto.

What we claim is:

1. A process for the preparation of alcohols by reaction of organic carbonyl compounds selected from the group consisting of ketones and aldehydes, or mixtures containing said organic carbonyl compounds, with hydrogen at an elevated temperature in the presence of a supported hydrogenation catalyst wherein said catalyst contains 20% to 90% by weight of nickel, based on said catalyst, 1 to 30 parts by weight of aluminum oxide per 100 parts by weight of said nickel, and 0.5 to 20 parts by weight of zirconium dioxide per 100 parts by weight of said nickel, said nickel, aluminum oxide, and said zirconium dioxide being coprecipitated on a support, said process comprising reacting said carbonyl compounds at 60° C. to 150° C., in the presence of said catalyst.

2. The process of claim 1 wherein said compounds are selected from the group consisting of aldehydes.

3. The process of claim 2 wherein said compounds are aliphatic aldehydes.

4. The process of claim 1 wherein said support is selected from the group consisting of activated charcoal, alumina, pumice, $\gamma$-$Al_2O_3$, precipitated silicic acid, silica gel, kieselguhr, and silicic earth.

5. The process of claim 4 wherein said support is selected from the group consisting of precipitated silicic acid, silica gel, kieselguhr, and silicic earth.

6. The process of claim 5 wherein said support is selected from the group consisting of precipitated silicic acid and kieselguhr.

7. The process of claim 1 wherein said support is present in a support amount of 6 to 80 parts by weight per 100 parts by weight of said nickel.

8. The process of claim 7 wherein said support amount is 15 to 65.

9. The process of claim 8 wherein said support amount is 35 to 50.

10. The process of claim 1 carried out in the liquid phase at a temperature of 60° to 150° C. and a pressure of 0.1 to 25 MPa.

11. The process of claim 10 wherein said temperature is 80° to 140° C. and said pressure is 1.0 to 15 MPa.

12. The process of claim 11 wherein said temperature is 90° to 130° C. and said pressure is 2.0 to 10 MPa.

13. The process of claim 1 carried out in the liquid phase at a space velocity of 0.6 to 2.0 volumes of liquid feed material/volume of said catalyst per hour.

14. The process of claim 13 wherein said space velocity is 0.8 to 1.6.

15. The process of claim 14 wherein said space velocity is 1.0 to 1.5.

16. The process of claim 1 carried out in the gaseous phase at temperatures of 60° to 150° C. and a pressure of 0.05 to 2.0 MPa.

17. The process of claim 16 wherein said temperature is 80° to 140° C. and said pressure is 0.1 to 1.2 MPa.

18. The process of claim 17 wherein said temperature is 90° to 130° C. and said pressure is 0.15 to 1.0 MPa.

19. The process of claim 16 carried out at a space velocity of 0.2 to 1.5 volumes of liquid feed material per volume of said catalyst per hour.

20. The process of claim 19 wherein said space velocity is 0.3 to 1.2.

21. The process of claim 20 wherein said space velocity is 0.5 to 1.0.

22. The process of claim 1 wherein said nickel, aluminum oxide, and zirconium dioxide are coprecipitated on said support.

* * * * *